US010586926B2

(12) United States Patent
Hartmann et al.

(10) Patent No.: US 10,586,926 B2
(45) Date of Patent: *Mar. 10, 2020

(54) OXOCARBON-, PSEUDOOXOCARBON- AND RADIALENE COMPOUNDS AND THEIR USE

(71) Applicant: Novaled GmbH, Dresden (DE)

(72) Inventors: Horst Hartmann, Dresden (DE); Olaf Zeika, Theissen (DE); Andrea Lux, Dresden (DE); Steffen Willmann, Dresden (DE)

(73) Assignee: Novaled GmbH, Dresden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/817,398

(22) Filed: Nov. 20, 2017

(65) Prior Publication Data
US 2018/0076389 A1 Mar. 15, 2018

Related U.S. Application Data

(62) Division of application No. 14/570,443, filed on Dec. 15, 2014, now Pat. No. 9,876,172, which is a division of application No. 14/080,340, filed on Nov. 14, 2013, now Pat. No. 8,911,645, which is a division of application No. 13/178,855, filed on Jul. 8, 2011, now Pat. No. 8,617,426, which is a division of application No. 12/111,326, filed on Apr. 29, 2008, now Pat. No. 7,981,324.

(30) Foreign Application Priority Data

Apr. 30, 2007 (EP) ..................... 07008747

(51) Int. Cl.
*H01L 51/00* (2006.01)
*C09B 11/02* (2006.01)
*C09B 47/04* (2006.01)
*C09B 57/00* (2006.01)
*C07C 255/51* (2006.01)
*C07C 261/04* (2006.01)
*C07D 333/24* (2006.01)
*C07C 255/31* (2006.01)
*C07C 255/40* (2006.01)
*C07D 213/53* (2006.01)
*C07C 325/02* (2006.01)
*C07C 49/39* (2006.01)
*C07C 49/395* (2006.01)
*C07C 49/653* (2006.01)
*C07C 13/04* (2006.01)
(Continued)

(52) U.S. Cl.
CPC ............ *H01L 51/005* (2013.01); *C07C 13/04* (2013.01); *C07C 13/06* (2013.01); *C07C 13/11* (2013.01); *C07C 13/19* (2013.01); *C07C 49/39* (2013.01); *C07C 49/395* (2013.01); *C07C 49/653* (2013.01); *C07C 255/31* (2013.01); *C07C 255/40* (2013.01); *C07C 255/51* (2013.01); *C07C 261/04* (2013.01); *C07C 325/02* (2013.01); *C07D 213/53* (2013.01); *C07D 333/24* (2013.01); *C09B 11/02* (2013.01); *C09B 47/04* (2013.01); *C09B 57/00* (2013.01); *C09B 57/008* (2013.01); *H01L 51/002* (2013.01); *H01L 51/0051* (2013.01); *C07C 2601/02* (2017.05); *C07C 2601/04* (2017.05); *C07C 2601/08* (2017.05); *C07C 2601/14* (2017.05); *C07C 2601/16* (2017.05); *H01L 51/0067* (2013.01); *H01L 51/0068* (2013.01); *Y02E 10/549* (2013.01); *Y02P 70/521* (2015.11)

(58) Field of Classification Search
CPC . H01L 51/002; H01L 51/005; H01L 51/0068; H01L 51/0051; H01L 51/0067; Y02E 10/549; H01B 1/12; C09B 57/008; C09B 57/00; C09B 47/04; C09B 11/02; C07D 213/53; C07D 333/24; Y02P 70/521; C09K 11/06; C07C 49/385; C07C 13/19; C07C 13/11; C07C 13/06; C07C 13/04; C07C 49/653; C07C 49/395; C07C 49/39; C07C 325/02; C07C 255/40; C07C 255/31; C07C 261/04; C07C 255/51; C07C 2601/16; C07C 2601/14; C07C 2601/08; C07C 2601/04; C07C 2601/02
USPC ............ 252/519.21, 500; 313/504; 558/434, 558/430; 546/330
See application file for complete search history.

(56) References Cited

U.S. PATENT DOCUMENTS 2,566,208 A   8/1951  Jenkins
3,083,242 A   3/1963  Ramsden
(Continued)

FOREIGN PATENT DOCUMENTS

CA   2549309   9/2005
CH    354065   5/1961
(Continued)

OTHER PUBLICATIONS

Akiba, Kin-Ya et al., "Direct Synthesis of 2,2-diaryl-3-methyl-2,3-dihydrobenzothiazoles from 3-methyl-2,3-dihydrobenzothiazole-2-thione and some mechanistic aspects," Bulletin of the Chemical Society of Japan, vol. 52(1), pp. 156-159, (1979).
(Continued)

*Primary Examiner* — Douglas J Mc Ginty
(74) *Attorney, Agent, or Firm* — Evershed Sutherland (US) LLP

(57) ABSTRACT

The present invention relates to oxocarbon-, pseudooxocarbon- and radialene compounds as well as to their use as doping agent for doping an organic semiconductive matrix material, as blocker material, as charge injection layer, as electrode material as well as organic semiconductor, as well as electronic components and organic semiconductive materials using them.

20 Claims, No Drawings

(51) Int. Cl.
*C07C 13/06* (2006.01)
*C07C 13/11* (2006.01)
*C07C 13/19* (2006.01)

(56) References Cited

U.S. PATENT DOCUMENTS

| | | | |
|---|---|---|---|
| 3,226,450 A | 12/1965 | Blazejak et al. | |
| 3,558,671 A | 1/1971 | Martin | |
| 3,563,751 A | 2/1971 | Cohen | |
| 3,963,769 A | 6/1976 | Fukunaga | |
| 4,003,943 A | 1/1977 | Fukunaga | |
| 4,005,091 A | 1/1977 | Fukunaga | |
| 4,066,569 A | 1/1978 | Lim | |
| 4,133,821 A | 1/1979 | West et al. | |
| 4,585,895 A | 4/1986 | Law | |
| 4,618,453 A | 10/1986 | Kim | |
| 4,769,292 A | 9/1988 | Tang et al. | |
| 4,960,916 A | 10/1990 | Pazik et al. | |
| 5,093,698 A | 3/1992 | Egusa | |
| 5,110,835 A | 5/1992 | Walter et al. | |
| 5,247,226 A | 9/1993 | Sato et al. | |
| 5,281,730 A | 1/1994 | Zambounis et al. | |
| 5,292,881 A | 3/1994 | Berneth et al. | |
| 5,393,614 A | 2/1995 | Nakada | |
| 5,556,524 A | 9/1996 | Albers | |
| 5,811,833 A | 9/1998 | Thompson | |
| 5,840,217 A | 11/1998 | Lupo et al. | |
| 5,922,396 A | 7/1999 | Thompson et al. | |
| 6,013,384 A | 1/2000 | Thompson et al. | |
| 6,013,982 A | 1/2000 | Thompson et al. | |
| 6,103,459 A | 8/2000 | Diel et al. | |
| 6,207,835 B1 | 3/2001 | Reiffenrath et al. | |
| 6,350,534 B1 | 2/2002 | Boerner et al. | |
| 6,423,429 B2 | 7/2002 | Kido et al. | |
| 6,524,728 B1 | 2/2003 | Kijima et al. | |
| 6,700,058 B2 | 3/2004 | Nelles et al. | |
| 6,747,287 B1 | 6/2004 | Toguchi et al. | |
| 6,824,890 B2 | 11/2004 | Bazan et al. | |
| 6,908,783 B1 | 6/2005 | Kuehl et al. | |
| 6,972,334 B1 | 12/2005 | Shibanuma et al. | |
| 7,081,550 B2 | 7/2006 | Hosokawa et al. | |
| 7,345,300 B2 | 3/2008 | Qin | |
| 7,807,687 B2 | 10/2010 | Salbeck et al. | |
| 7,972,541 B2 * | 7/2011 | Werner | H01L 51/002 252/519.2 |
| 7,981,324 B2 | 7/2011 | Hartmann et al. | |
| 8,057,712 B2 * | 11/2011 | Zeika | C07C 255/35 252/500 |
| 8,460,581 B2 * | 6/2013 | Hartmann | C07D 207/44 252/500 |
| 8,617,426 B2 * | 12/2013 | Hartmann | H01L 51/002 252/500 |
| 8,911,645 B2 * | 12/2014 | Hartmann | H01L 51/002 252/500 |
| 8,951,443 B2 * | 2/2015 | Werner | C09K 11/06 136/263 |
| 9,028,979 B2 * | 5/2015 | Schildknecht | C07D 235/02 257/40 |
| 9,048,435 B2 * | 6/2015 | Werner | H01L 51/006 |
| 9,876,172 B2 * | 1/2018 | Hartmann | H01L 51/002 |
| 2003/0064248 A1 | 4/2003 | Wolk | |
| 2003/0165715 A1 | 9/2003 | Yoon et al. | |
| 2003/0234397 A1 | 12/2003 | Schmid et al. | |
| 2004/0068115 A1 | 4/2004 | Lecloux et al. | |
| 2004/0076853 A1 | 4/2004 | Jarikov et al. | |
| 2005/0040390 A1 | 2/2005 | Pfeiffer et al. | |
| 2005/0061232 A1 | 3/2005 | Werner et al. | |
| 2005/0072971 A1 | 4/2005 | Marrocco et al. | |
| 2005/0086251 A1 | 4/2005 | Hatscher et al. | |
| 2005/0110009 A1 | 5/2005 | Blochwitz-Nimoth et al. | |
| 2005/0121667 A1 | 6/2005 | Kuehl et al. | |
| 2006/0049397 A1 | 3/2006 | Pfeiffer et al. | |
| 2007/0026257 A1 | 2/2007 | Begley et al. | |
| 2007/0058426 A1 | 3/2007 | Sokolik et al. | |
| 2007/0090371 A1 | 4/2007 | Drechsel et al. | |
| 2007/0116984 A1 | 5/2007 | Park et al. | |
| 2007/0145355 A1 | 6/2007 | Werner et al. | |
| 2007/0218335 A1 | 9/2007 | Yoshimura | |
| 2007/0252140 A1 | 11/2007 | Limmert et al. | |
| 2008/0103315 A1 | 5/2008 | Egawa et al. | |
| 2008/0122345 A1 | 5/2008 | Sakata et al. | |
| 2008/0145708 A1 | 6/2008 | Heil et al. | |
| 2008/0265216 A1 | 10/2008 | Hartmann et al. | |
| 2009/0001327 A1 | 1/2009 | Werner et al. | |
| 2010/0026176 A1 | 2/2010 | Blochwitz-Nomith et al. | |
| 2010/0102709 A1 | 4/2010 | Zeika et al. | |
| 2013/0193414 A1 | 8/2013 | Werner et al. | |
| 2015/0001505 A1 * | 1/2015 | Kawamura | C07C 255/34 257/40 |
| 2018/0315928 A1 * | 11/2018 | Hayashi | H01L 51/50 |

FOREIGN PATENT DOCUMENTS

| | | |
|---|---|---|
| CH | 354066 | 5/1961 |
| DE | 19836408 | 2/2000 |
| DE | 10261662 | 7/2004 |
| EP | 1000998 | 5/2000 |
| JP | 61254582 | 11/1986 |
| JP | 63172274 | 7/1988 |
| JP | 63172275 | 7/1988 |
| JP | 04338760 | 11/1992 |
| JP | 2004002740 | 1/2004 |
| JP | 2004002741 | 1/2004 |
| JP | 2004010703 | 1/2004 |
| JP | 2004335557 | 11/2004 |
| JP | 07-168377 | 7/2007 |
| JP | 2004100621 | 5/2010 |
| WO | WO 2003/088271 | 10/2003 |
| WO | WO 2003/104237 | 12/2003 |
| WO | WO 2006/067800 | 6/2006 |
| WO | WO 2008/022633 | 2/2008 |
| WO | WO 2011131185 | 10/2011 |

OTHER PUBLICATIONS

Akutagawa, T. et al. "Multi Electron and Proton-Transfer System Based on 2,2'-biimidazole derivatives," Science and Technology of Syn. Metals, 1994, 346.

Alonso, R. A. et al. "Photostimulated Reaction of Diphenylarsenide and Diphenylstibide Ions with Haloaromatic Compounds by the Srnl Mechanism. Electron Transfer vs. Bond Breaking of the Radical Anion Intermediate," J. Org. Chem. (1982) 47(1) pp. 77-80.

Bach, U. et al. "Solid-state dye-sensitized mesoporous $TiO_2$ solar cells with high photon-to-electron conversion efficiencies," Nature, vol. 395, Oct. 8, 1998, pp. 583-585.

Bamgboye, T.T. et a. "Lewis acidity of $Ph2SbX3$, wherein X = Cl or Br. Crystal structures of $Ph2SbC13*H2O$ and $Ph2SbBr3*MeCN$," J. of Organometallic Chem. vol. 362, Feb. 28, 1989, pp. 77-85.

Bard, A. J., Faulkner, R.J., Electrochemical Methods: Fundamentals and Applications, Wiley, 2nd Ed., 2000 (Chapter 6).

Barton, D.H.R. et al. "Comparative Arylation Reactions with Pentaphenylbismuth and with Triphenylbismuth Carbonate," J. Chem. Soc. Chem. Commun. (1980) 17, pp. 827-829.

Baumgartel, H. et al., "Polarographische Untersuchungen zur Konformation von 1.2.3.4.5-pentaarylimidazoliumkationen," Ber. Bunsenges (1972) 76/2, 94-100.

Baumgartel, H. et al.,"Uber eine neue Synthese von tetraaryl-imidazolen and pentaaryl-imidazolium-salzen," Chem. Ber. (1968), 101, 3504.

Bhattacharya, S.N. et al. "Preparation & Characterization of Some Triarylarsenic & Triarylantimony Mixed Halides & Related Compounds," Indian J. Chem. 16A (1978) pp. 778-781.

Bonati, F. et al. "Reactions of C-imidazolyllithium derivatives with Broup Ib compounds: tris[micro-(1-alkylimidazolato-N3, C2)]tri-gold (I) and -silver (I)," J. Organomet. Chem. 1989, 375, pp. 147-160.

Brucsis, L. et al. "Substituionasreaktionen an 1,4-dihalogen-2,3,5,6-tetracyan-benzolen," Chem. Ber. 109(1976) pp. 2469-2474.

Cherkashin M. I. et al. "Studies on 2,4,5-triarylimidazoles," Izv. Akad. Nauk SSSR, Seriya Khim. 1982, 2, pp. 376-377.

(56) References Cited

OTHER PUBLICATIONS

Curini, M. et al., "Ytterbium Triflate Promoted Synthesis of Benzimidazole Derivatives," Synlett, No. 10, pp. 1832-1834, 2004.
Dedik, S.G. et al. "Tetrahalotetraazafulvalenes-new strong electron acceptors," Chemistry of Heterocyclic Compounds (a Translation of Khimiyageterotsiklicheskikh Soedinenii), Plenum Press Co., New York, U.S., vol. 10, Jan. 1, 1989, p. 1421.
Deluca, Mark et al., "The p-toluenesulfonic acid promoted synthesis of 2-substituted benzoxazoles and benzimidazoles from diacylated precursors," Tetrahedron, vol. 53, No. 2, pp. 457-464, 1997.
Endo, Jun et al., "Organic Electroluminescent Devices with a vacuum-deposited Lewis Acid doped hole injecting layer," Japan Society of Applied Physics, vol. 41, 2002, pp. L358-L360, Part 2, No. 3B, Mar. 15, 2002.
Fausett, B.W. et al. "Palladium-catalyzed coupling of thiol esters with aryl and primary and secondary alkyl organiindium reagents," J. Org. Chem. (2005) 70(12) pp. 4851-4853.
Fenghong Li et al., "Leuco Crystal Violet as a dopant for n-doping of organic thin films of fullerene C60," J. Phys. Chem. B 2004, 108, pp. 17076-17088.
Fild, Manfred et al. "Group VA pentafluorophenyl compounds. 14. Pentafluorophenyl-substituted phosphoranes," Zeitschrift Fuer Anorganische und Allgemeine Chemie, 439, pp. 145-152 (1978).
Gan, F. "Optical nonlinearity of hybrid and nanocomposite materials prepared by the Sol-Gel method," J. of Sol-Gel Science and Technology, 13, 559-563 (1998).
Ganzorig, C. et al., "p-Typed Semiconducts of Aromatic Diamines Doped with SbC15," Chemistry Letters 2000, pp. 1032-1033.
Gibbons, M.N. et al. "Multiply Bridged Diantimony Compounds," Phosphorus, Sulfur, & Silicon 93/94 (1994).
Giovanella, et al. "Electroluminescence from two fluorinated organic emitters embedded in polyvinyl carbazole," Applied Physics Letters, vol. 87, pp. 171910-1-171910-3.
Glemser, O. et al. "Synthese von Tris-pentafluorphenylarsin, -stibin und -phosphin sowie von Trimethyl-pentafluor-phenylsilan," Angew. Chemie (1964) 76, 953.
Gogoi, P. et al. "An efficient and one-pot synthesis of imidazolines and benzimidazoles via anaerobic oxidation of carbon-nitrogen bonds in water," Tetrahedron Lett. 2006, 47, pp. 79-82.
Gregg, B.A. et al., "On the superlinear increase in conductivity with dopant concentration in excitonic semiconductors," Applied Physics Letters, vol. 84, No. 10, Mar. 8, 2004, pp. 1707-1709.
Grimmett, M. R., "Imidazole and benzimidazole synthesis," Tables of Contents, pp. 1-10, Academic Press, Harcourt Brace & Company, Publishers, London, San Diego, NY, Boston et al., 1997.
Gufeng, He et al., "High-efficiency and low-voltage p-i-n. electrophosphorescent organic light-emitting diodes with double-emission layers," Applied Physics Letters, vol. 85, No. 17, 2004-10-25, pp. 3911-3913.
Haddon, R.C. et al., "Conducting films of C60 and C70 by alkali-metal doping," Nature, vol. 350, Mar. 28, 1991, pp. 320-322.
Harada, Kentaro et al., "Realization of organic pn-homojunction using a novel n-type doping technique, Proceedings of SPIE—The international Society for Optical Engineering; Organic Optoelectronics and Photonics 2004," vol. 5464, Sep. 2004, pp. 1-9.
Harris, G. S. et al."The Reaction of Trispentafluorophenylstibine with Halogens and Interhalogens," J. Fluorine Chem. 37 (1987) pp. 247-252.
Heinze, J. et al., "Polarographic studies of the conformation of 1,2,3,4,5-pentaarylimidazolium cations," The Institute for Physical Chemistry at the University of Freiburg, pp. 1-22, 1972.
Hill, J. "Oxidative Dimerization of Benzimidazole," J. Org. Chem. 1963, 28, pp. 1931-1932.
Japp, F. et al. "Constitution of Glycosine," J. Chem. Soc. Trans. 1887, 51, pp. 552-557.
Jefferson, Alan M. and Suschitzky, H., "New Route to Nucleophilically Substituted o-phenylenediamines," J.C.S. Chem. Comm. pp. 189-190, 1997.
Jensen, W.B.; The Generalized Lewis Acid Based Concepts, John Wiley & Sons, New York, 1980, pp. 113-195.
Ji, L. et al. "Mono-, di- and tetra-nuclear ruthenium (II) complexes containing 2,2'-p-phenylenebis(imidazo[4,5-f]phenanthroline): synthesis, characterization and third-order non-linear optical properties," J. Chem. Soc., Dalton Trans. 2001, pp. 1920-1926.
Katz, H.E. et al., "Pyridyl Dicyanoquinodimethane Acceptors for Electroactive Solids," J. Org. Chem. 56 (1991) pp. 5318-5324.
Kaufhold, Von Jurgen et al., "Uber das Leitfahigkeitsverhalten verschiedener Phthalocyanine im Vakuum und unter dem Einfluss von gasen," Ber. Bunsen. Phys. Chem. 69, pp. 168-179.
Kikuchi, A et al. "A new family of pi-conjugated delocalized biradicals: electronic structures of 1,4-bis(2,5-diphenylimidazol-4-ylidene)cyclohexa-2,5-diene," J. Phys. Chem. B., 2005, 109, pp. 19448-19453.
Kikuchi, A. et al. "Definitive Evidence for the Contribution of Biradical Character in a Closed-Shell Molecule, Derivative of 1,4-Bis-(4,5-diphenylimidazol-2-ylidene)cyclohexa-2,5-diene," J. Am. Chem. Soc. 2004, 126, pp. 6526-6527.
Kimura, M. et al. "Preparation of 4-(4,5-diphenyl-1H-imidazol-2-yl)benzaldehyde and Its Practical Synthetic Use in the Synthesis of Unsymmetrically Substituted Imidazoles," ITE Letters on Batteries, New Technologies and Medicine, 2002, 3, pp. 30-34.
Klopman, G. "Chemical Reactivity and the Concept of Charge-and Frontier-controlled reactions," Journal of the American Chemical Society., vol. 90, No. 2, Jan. 17, 1968, pp. 223-234.
Kozaki, M. et al. "Preparation, Properties, and Reduction of Heteroaromatic Quinoids with 1,4-diazacyclopentadien-2-ylidene Terminals," Org. Lett. 2005, 7, pp. 115-118.
Krebs, F.C. et al. "Superradiant properties of 4,4'-bis(1H-phenanthro[9,10-d]imidazol-2-yl)biphenyl and how a laser dye with exceptional stability can be obtained in only one synthetic step," Tetrahedron Lett. 2001, 42, pp. 6753-6757.
Kulkarni, A.P. et al., "Electron transport materials for organic light-emitting diodes," Chem. Mater. 2004, 16, pp. 4556-4573.
Lane, E.S. "A Modified Benziminazole Synthesis," J. Chem. Soc. 1953, pp. 2238-2240.
Lehmstaedt, K. et al. "Halogen-2,2'-diimidazole und ihre Umsetzungen mit Aminen zu Farbstoffen," Ber. Dt. Chem. Ges. B, 1943, pp. 879-891.
Leyden, R. et al. "Thermally Induced Degradation of 2,3,5,6-tetrachloroterephthalylidenebis(o-aminoaniline)," J. Org. Chem. 1983, 48, pp. 727-731.
Li, J. Y. et al. "Enhancement of green electroluminescence from 2,5-di-p-anisyl-isobenzofuran by double-layer doping strategy," Preparation and Characterization, vol. 446, No. 1, pp. 111-116.
Ludvik, J. and Pragst, F. et al., "Electrochemical generation of triplet states," Journal of Electroanalytical Chemistry, No. 180, pp. 141-156, (1984).
Ludvik, J. and Volke, J. "Evidence for a radical intermediate in the anodic oxidation of reduced nicotinamide adenine dinucleotides obtained by electrogenerated chemiluminescence," Analytica Chimica Acta, 209 (1988) 69-78.
Maennig, B. et al., "Organic p-i-n solar cells," App. Phys. 2004, A 79, pp. 1-14.
Matschke, M. et al. "Bis-4h-imidazoles-tetraazafulvalenes-2,2'-biimidazoles: three variations of one redox system," Tetrahedron, vol. 62, No. 36, Sep. 4, 2006, pp. 8586-8590.
Mayer, U. et al. "Uber 2,3,6,7-tetraphenyl-1,4,5,8-tetraazafulvalen," Tetrahedron Lett. 1966, 42, pp. 5221-5223.
Mayer, U. et al. "Uber Biradikale, Chinone and Semichinone der Imidazolyl-Reihe," Angew. Chem. 1966, 78, p. 303.
Minoura, M. et al. "Hexaaryltellurium, the First Neutral Compounds Comprising Hexarylated Elements," Angew. Chem. Int. Edit. 35 (22) pp. 2660-2662 (1996).
Miyasato, M. et al. "Syntheses and Reactions of Hexavalent Organitellurium Compounds Bearing Five or Six Tellurium-Carbon Bonds," Chem.—A European J. 10(10) pp. 2590-2600 (2004).
Muramatsu, T. et al, "Visible Light Sensitive Cyclomer and Its Tautomeric Dispiro Compound Formed from Bispyridiny Diradical," J. Am. Chem. Soc. 2005, 127, 4572-3.
Muramatsu, T. et al., "Photosensitive Cyclomer Formation of 1,1'-(1,2-ethanediyl)bis(pyridinyl) diradical and its derivativese," J. Am. Chem. Soc. 1989, 111, 5782-7.

(56) References Cited

OTHER PUBLICATIONS

Muramatsu, T. et al., "Preparation and Properties of a novel heterocyclic dispiro compound, 3, 10-diaza-N,N-dimethyldispiro[5.0.5.3]pentadeca-1,4,8,11-tetraene," Chemistry Letters, pp. 151-152, (1996).
Nelsen, Stephen, F.; "Heterocyclic Radical Anions. II. Naphthalic and 1,4,5,8-Naphthalenetetracarboxylic Acid Derivatives," Journal of the American Chemical Society, 89:23, Nov. 8, 1967, pp. 5925-5931.
Oeter, D. et al., "Doping and Stability of Ultrapure alpha-oligothiophene Thin Films," Synthetic Metals, 61, 1993, pp. 147-150.
Okada, K. et al. "Detection of a diradical intermediate in the cis-trans isomerization of 5,5'-bis(4,5-diphenyl-2H-imidazol-2-ylidene)-5,5'-dihydro-delta 2,2'-bithiophene," Tetrahedron Lett. 2006, 47, pp. 5375-5378.
Okada, K. et al. "Novel Dimers of 2,2'-(m-Phenylene)bis(4,5-diphenyl-1-imidazolyl) Diradical," Chem. Lett. 1998, pp. 891-892.
Otero, A. et a. "Pentachlorophenyl-arsenic, -antimony and -bismuth compounds," J. of Organometallic Chemistry, vol. 171, No. 3, Jan. 1, 1979, pp. 333-336.
Otero, A. et al. "Pentafluorophenylantimony compounds," J. Organometallic Chem. 154 (1978) pp. 13-19.
Ouchi, A. et al. "13C-nuclear magnetic resonance of some triaryl- and tri-alkylantimony and -bismuth derivatives," J. of Inorganic and Nuclear Chemistry, vol. 37, Issue 11, Nov. 1975, pp. 2347-2349.
Ouchi, A. et al. "The syntheses and properties of some alkylthioacetato and arylthioacetato derivatives of triphenylantimony(V) and -bismus (V)," J. of Inorganic and Nuclear Chemistry, vol. 37, Issue 12, Dec. 1975, pp. 2559-2561.
Park, S. B. et al. "Highly Efficient, Recyclable Pd(II) Catalysts with Bisimidazole Ligands for the Heck Reaction in Ionic Liquids," Organic Lett. 2003, 5, pp. 3209-3212.
Parthasarathy, G. et al., "Lithium doping of semiconducting organic charge transport materials," J. Appl. Phys., vol. 89, No. 9, May 1, 2001, pp. 4986-4992.
Petzhold, C. "Beitrage zur Synthese funktioneller 1,4,5,8-tetraazafulvalene," Dissertation; Friedrich-Schiller-Universitat Jena; 2006.
Quast, H. and Schmitt, E.; "Note Regarding the Quaternization of Heterocycles," Institute of Organic Chemistry at the University of Wurzburg, Chem. Ber. 101, pp. 4012-4014, (1968).
Rake, A. T. et al. "Pentafluorophenyl and phenyl-phosphinidene ions and their group V analogues," Oms. Organic Mass Spectrometry, vol. 3 Jan. 1, 1970, pp. 237-238.
Rasmussen, P.G. et al. "Complexes of the New Ligand Tetracyanobiimidazole," J. Am. Chem. Soc. 1982, 104, pp. 6155-6156.
Rezende, M. C. et al. "An Alternative Preparation of Bisbenzimidazoles," Syn. Comm. 2001, 31, pp. 607-613.
Rezende, M. et al. "Puzzling Formation of Bisimidazole Derivatives from Hexachloroacetone and Diamines," Tetrahedron Lett. 1996, 37, 5265-5268.
Sakaino, Y. "Structures and Chromotropic Properties of 1,4-bis(4,5-diphenylimidazol-2-yl)benzene Derivatives," J. Org. Chem. 1979, 44, pp. 1241-1244.
Sato, S. et al. "Isolation and Molecular Structure of the Organopersulfuranes [12-S-6(C6)]," J. Am. Chem. Soc. 128(21) pp. 6778-6779 (2006).
Schneiders, P. et al. "Notiz zur Darstellung von 4,4',5,5'-tetrasubstituierten Di-2-imidazolyl-derivaten. Ausgangsprodukte zur Darstellung von 1,4,5,8-tetraazafulvalenen," Chem. Ber. 1973, 106, pp. 2415-2417.
Schwarz, W. M. et al., "Formation of Stable Free Radicals on Electroreduction of N-alkylpyridium salts," J. Am. Chem. Soc., 33 3164 (1961).
Sekine, T. et al. "Dimerizations of pi-Rich N-heteroaromatic compounds and xanthine derivatives," Chem. Pharm. Bull. 1989, 37, pp. 1987-1989.

Sharma, G.D. et al., "Influence of Iodine on the Electrical and Photoelectrical Properties of Zinc Phthalocyanine Think Film Devices," Materials Science and Engineering, B41, 1996, pp. 222-227.
Singhal, K. et al. "On the Lewis acidity of tris(pentafluorophenyl)antimony (V) dichloride towards neutral monodentate O, N and S donor ligands," Journal of Fluorine Chemistry, vol. 121, No. 2, Jun. 1, 2003, pp. 131-134.
Smith, M.B. Organic Synthesis, McGraw-Hill, Inc. 1994, Chapter 1.
Sprenger, et al. "The cyclobutenediylium cation, a novel chromophore from squaric acid," Angew. Chem. International Edition, vol. 6 (1967), No. 6, pp. 553-554.
Suschitzky, H. "Syntheses and Reactions of 2,2'-bisbenzimidazole Systems," J. Heterocyclic Chem. 1999, 36, pp. 1001-1012.
Suzuki, T. et al., "4,7-bis(dimethylamino)benzimidazoles and twin-type derivatives: reversible two-stage redox system modulated by proton-transfer," Tetrahedron Lett. 2003, 44, pp. 7881-7884.
Vaid T.P. et al., "Investigations of the 9,10-diphenylacridyl radical as an isostructural dopant for the molecular semiconductor 9, 10-diphenylanthracene," Chemistry of Materials, American Chemical Society, Bd. 15, Nr. 22, 4292-4299 (2003).
Vyas, P.C. et al. "A simple synthesis of 2,2'-bis-benzimidazoles," Chem. Industry, 1980, pp. 287-288.
Weiss, M. "Acetic Acid-Ammonium Acetate Reactions. 2-Isoimidazoles as Intermediates in Imidazole Formation," J. Am. Chem. Soc. 1952, 74, pp. 5193-5195.
Wintgens, V. et al., "Reduction of Pyrylium Salts: Study by ESR and UV_Visible Spectroscopy of the Reversible Dimerization of the Pyranyl Radical," New. J. Chem., 10/6, 345-350 (1986).
Yamaguchi, et al., "New Approaches to Tetracyanoquinodimethane," Bull. Chem. Soc. Jpn. 62 (1989) pp. 3036-3037.
Yamamoto, Y. et al. "The Electrical Properties of the Poly(N-vinyl Carbazole)-Antimony (V) Chloride (or Iodine) Charge Transfer Complexes," Bull. Chem. Soc. Jap. 1965, 38, 2015-2017.
Yoshiko, S., et al. "The Quinoid-biradical Tautomerism of 3,6-bis(4,5-diphenyl-2H-imidazol-2-ylidene)-1,4-cyclohexadiene," Nippon Kagaku Kaishi, 1972, 1, pp. 100-103.
Yukihiko, T., et al. "Studies on Aromatic Nitro Compounds. V. A Simple One-Pot Preparation of o-Aminoaroylnitriles from Some Aromatic Nitro Compounds," Chem. Pharm. Bull., 33 (4) 1360-1366 (1985).
Zhou, X et al., "Enhanced hole Injection Into Amorphous Hole-Transport Layers of Organic Light-Emitting Diodes Using Controlled p-Type Doping," Adv. Funct. Mater., 2001, 11, No. 4, pp. 310-314.
English Translation of Japanese Office Action; Japanese Patent Application No. 2005-228491; dated Apr. 17, 2009.
International Search Report, International App. No. PCT/EP2007/002359, dated May 24, 2007.
Final Office Action, U.S. Appl. No. 11/688,777; dated Nov. 27, 2009.
Non-Final Office Action, U.S. Appl. No. 11/688,777; dated Feb. 2, 2009.
Response to Office Action, U.S. Appl. No. 11/688,777; dated Sep. 4, 2009.
Response to Office Action, U.S. Appl. No. 11/688,777; dated Aug. 3, 2009.
Restriction Requirement, U.S. Appl. No. 11/688,777; dated Mar. 5, 2010.
Response to Restriction Requirement, U.S. Appl. No. 11/688,777; dated Apr. 1, 2010.
Notice of Allowance, U.S. Appl. No. 11/196,491; dated Apr. 13, 2009.
Notice of Allowance, U.S. Appl. No. 11/196,491; dated Oct. 20, 2008.
Response to Office Action for U.S. Appl. No. 11/196,491; dated Aug. 11, 2008.
Final Office Action, U.S. Appl. No. 11/196,491; dated Feb. 11, 2008.
Response to Office Action for U.S. Appl. No. 11/196,491; dated Nov. 5, 2008.
Non-Final Office Action, U.S. Appl. No. 11/196,491, dated Jul. 3, 2007.
International Search Report and Preliminary Report on Patentability for PCT/DE2008/001080; dated Jul. 11, 2008.

(56) References Cited

OTHER PUBLICATIONS

International Search Report for PCT/DE2008/00654; dated Jun. 15, 2009.
International Search Report and Preliminary Report on Patentability for PCT/EP2006/010816; dated Feb. 9, 2007.
Advisory Action for U.S. Appl. No. 11/315,072 dated Mar. 8, 2010.
Response to Final Office Action for U.S. Appl. No. 11/315,072; dated Feb. 17, 2010.
Final Rejection for U.S. Appl. No. 11/315,072; dated Nov. 16, 2009.
Response to Office Action for U.S. Appl. No. 11/315,072; dated Jul. 29, 2009.
Non-Final Rejection for U.S. Appl. No. 11/315,072; dated Apr. 29, 2009.
Non-Final Rejection for U.S. Appl. No. 11/315,072; dated Nov. 12, 2008.
Response to Office Action for U.S. Appl. No. 11/315,072; dated Feb. 10, 2009.
European Search Report for EP 07009366; dated Oct. 19, 2007.
International Search Report for PCT/EP2008/003792; dated Sep. 2, 2008.
Anderson, J.D. et al., "Electrochemistry and Electrogenerated Chemiluminescence Processes of the Componenets of Aluminum Quinolate/Triarylamine, and Related Organic Light emitting Diodes," J. Am. Chem. Soc., 1998, 120, pp. 9646-9655.
Gao, W. et al., "Effect of electrical doping on molecular level alignment at organic-organic heterojunctions," Applied Physics Letters, vol. 82, No. 26, Jun. 30, 2003, pp. 4815-4817.
Harada, K. et al. "Organic Homojunction Diodes with a High Built-in Potential: Interpretation of the Current-Voltage Characteristics by a Generalized Einstein Relation," Phys. Rev. Lett. 94, 036601 (2005).
Huang, Jingsong et al., "Low-voltage organic electroluminescent devices using pin structures," Applied Physics Letters, vol. 80, No. 1, Jan. 7, 2002, pp. 139-141.
Maitrot, M. et al., "Molecular material based junctions: Formation of a Schottky Contact with Metallophthalocyanine Thin Films Doped by the Cosublimation Method," J. Applied Physics, 60(7), Oct. 1, 1986, pp. 2396-2400.
Miller, L.L. et al., "A simple comprehensive correlation of organic oxidation and ionization potentials," J. Org. Chem., 1972, vol. 37, No. 6, pp. 916-918.
Nollau, A. et al., "Controlled n-type doping of a molecular organic semiconductor: naphthalenetetracarboxylic dianhydride (NTCDA) doped with bis(ethylenedithio)-tetrathiafulvalene (BEDT-TTF)," J. Appl. Phys., vol. 87, No. 9, May 1, 2006, pp. 4340-4343.
Parker, "On the Problem of Assigning Values to Energy Changes of Electrode Reactions," Journal of the American Chemical Society, 96:17, Aug. 21, 1974, pp. 5656-5661.
R. Schlaf et al., "Homo/Lumo Alignment at PTCDA/ZnPc and PTCDA/ClInPc Heterointerfaces Determined by Combined UPS and XPS Measurements," J. Phys. Chem. B 1999, 103, pp. 2984-2992.
Tang, T.B. et al., "Ionization thresholds of merocyanine dyes in the solid state," Journal of Applied Physics, vol. 59, (1), Jan. 1986, pp. 5-10.
Werner, A. G. et al., "Pyronin B as a donor for n-type doping of organic thin films," Applied Physics Letters, vol. 82, No. 25, Jun. 23, 2003, pp. 4495-4497.
Yao, Fu et al., "Quantum-chemical predictions of Absolute standard redox potentials of diverse organic molecules and free radicals in acetonitrile," J. Am. Chem. Soc. 2005, 127, pp. 7227-7234.
Zhou, X. et al., "Very low operating voltage organic light-emitting diodes using a p-doped amorphous hole injection layer," Applied Physics Letters, vol. 78, No. 4, Jan. 22, 2001, pp. 410-412.
Zimmerman, T. et al. "Benzocycloalkenone und dihydro-2H, 7H-1-benzopyranone aus 2,4,6-triaryl-pyryliumsalzen und cycloalkan-1,2-dionen," J. Prakt. Chem. 331 pp. 306-318 (1989).
Non-Final Rejection for U.S. Appl. No. 12/046,620; dated Nov. 25, 2009.
Response to Restriction Requirement for U.S. Appl. No. 12/046,620; dated Aug. 24, 2009.
Restriction Requirement for U.S. Appl. No. 12/046,620; dated Jul. 22, 2009.
Disclosure Statement Under 37 C.F.R. § 1.56 for U.S. Appl. No. 12/111,326 Submitted Herewith.
Bard, A. J., Faulkner, R.J., Electrochemical Methods: Fundamentals and Applications, Wiley, 2nd Ed., 2000 (Chapter 2).
D'Andrade, B.W. et al., "Relationship between the ionization and oxidation potentials of molecular organic semiconductors," Organic Electronics 6, 2005, pp. 11-20.
Kido, Junji et al., "Bright Organic Electroluminescent Devices Having a Metal-doped Electron-injecting Layer," Applied Physics Letters, vol. 73, No. 20, Nov. 16, 1998, pp. 2866-2868.
Pfeiffer, M, et al., "Doped Organic semiconductors: physics and application in light emitting diodes," Organic Electronics, Elsevier, Amsterdam, NL, vol. 4, No. 2/3, Sep. 2003 (Sep. 2003), pp. 89-103, XP001177135, ISSN: 1556-1199.
Tang, C.W. et al., "Organic electroluminescent diodes," Applied Physics Letters, vol. 51, No. 12, Sep. 21, 1987, pp. 913-915.
Iyoda et al., Novel synthesis of hexaaryl[3]radialenes via dibromo[3]dendralenes; Tetrahedron Letters 41 (2000, 6 pgs.
Chonan et al., "The Synthesis of Difluoro and Dimethyl Derivatives of 2,6-Bis(dicyanomethylene) . . . "; The Chemical Society of Japan (2004), pp. 1487-1497.
Ziegenbein et al., "The Cyclobutenediylium Cation, a Novel Chromophone from Squaric Acid," Angew. Chem. 79:12, pp. 581-582 (1967).
Kazuka et al., "Novel Electron Acceptors for Organic Conductors: 1,2-Bis(p-benzoquino)-3-[2-(dicyanomethylene)-2,5-thienoquino]cyclopropane Derivatives," J. Chem. Soc. Commun., pp. 519-520 (1994).
Fatiadi et al., "Electrochemical Oxidation of Serval Oxocarbon Salts in N—N-Dimethylformamide," J. Electroanal. Chem., 135 pp. 193-209 (1982).
Fatiadi, "Synthesis of 1,3-(Dicyanomethylene)croconate salts. New bond-delocalized dianion, Croconate Violet," J. Amer. Chem. Soc. 100:8, pp. 2586-2588 (1978).
Fatiadi, "Pseudooxocarbons. Synthesis of 1,2,3-Tris(dicyanomethylene)croconate Salts. A New Bond-Delocalized Dianion, Croconate Blue," J. Org. Chem., 45 pp. 1338-1339 (1980).
Blochwitz et al., "Low Voltage Organic Light Emitting Diodes Featuring Doped Phthalocyanine as Hole Transport Material," Appl. Phys. Lett. 73(6), pp. 729-731 (1998).
Fukunaga, "Negatively Substituted Trimethylenecyclopropane Dianions," J. Amer. Chem. Soc., 98, pp. 610-613 (1976).
Takahashi et al., "Novel Metallic Charge-Transfer Complexes Composed of a [3]Radialene Type Acceptor: A 1,2-bis(p-benzoquino)-3-[2-(dicyanomethylen) . . . ," Advanced Materials, Jul., No. 7, 3 pgs (1995).
Pfeiffer et al., "Controlled Doping of Phthalocyanine Layers by Cosublimation with Acceptor Molecules: A Systematic Seebeck and Conductivity Study," Appl. Phys. Lett., 73 (22) pp. 3202-3204 (1998).
West et al., "Diquinocyclopropanones, Diquinoethylenes, and the Anion-Radical and Free-Radical Intermediates in Their Formation," J. Org. Chem. 40:16, pp. 2295-2299 (1975).
Koster et al., "Synthesis and Reactions of a Tetraquinocyclobutane," J. Org. Chem., 40:16, pp. 2300-2304 (1975).
Blinka et al., "Octacyanotetramethylenecyclobutane Dianion and its Anion-Radical," Tetrahedron Lett., 24:15, pp. 1567-1568 (1983).
Hopf et al., "Preparation and Properties, Reactions, and Applications and Radialenes," Angew. Chem., 1992, vol. 31, No. 8, pp. 931-954 (1992).
Hopff et al., "Lieber Einen Neuen Kohlenwasserstoff C18-H24 (Hexaaethylidencyclohexan)," Chim. Acta, 46, pp. 380-386 (1961).
Seitz et al., "Eine Neue Synthesis und di Kristallstrukturanalyse von 'Krokonat-Blau', 1,2,4-Tis(dicyanmethylen)krokonat," Chem. Ber., 120, pp. 1691-1694 (1987).
Seitz et al., "Pseudooxokohlenstoffe," Nachr. Chem. Tech. Lab., 28:11, pp. 804-807 (1980).
Schmidt, "Reaktionen von Quadratsaeure und Quadratsaeure Derivaten," Synthesis, Dec., 24 pgs. (1980).

(56) References Cited

OTHER PUBLICATIONS

Japanese Office Action dated Apr. 2, 2013 for JP Application No. 2008-117346 (English translation) (5 pages).
Giovanella, et al. "Electroluminescence from two fluorinated organic emitters embedded in polyvinyl carbazole," Appl. Phys. Lett. vol. 87, p. 171910; date of publication: Oct. 18, 2005.
Kaufhold, et al. "Uber das Leitfahigkeitsverhalten verschiedener Phthalocyanine im Vakuum und unter dem Einfluss von gasen," Ber. Bunsen Phys. 69, pp. 168-179; date of publication: 1965.
Li, J.Y., "Enhancement of green electroluminescence from 2,5,-di-p-anisyl-isobenzofuran by double layer doping strategy," Thin Solid Films 446 (2004) 111-116; date of publication: 2004.
Korean Office Action for Korean Application No. 10-2008-0040353 dated Nov. 17, 2014.
Indian Office Action for IN Application No. 933/MUM/2008 dated Aug. 14, 2017 (4 pages).
European Office Action for EP Application No. 16169129.0 dated Sep. 5, 2017 (5 pages).
Karpov et al., "High Conductivity in Molecularly p-Doped Diketopyrrolopyrrole-Based Polymer: The Impact of a High Dopant Strength and Good Structural Order," Adv. Mater., 2016, pp. 1-8.
Hidemitsu Uno et al., "Re-Investigation of the Coupling Reaction of 2-Aryl-1, 1-dibromo-3,3,3-trifluoropropenes. Preparation of Perfluoroalkylated [3] Cumulenes," Bull. Chem. Soc. Jpnl, 72, 1365-1375 (1999).
First Examination Report of the Indian Patent Office for Indian Patent Application No. 201825017087, dated Nov. 27, 2019 (English translations included).

* cited by examiner

OXOCARBON-, PSEUDOOXOCARBON- AND RADIALENE COMPOUNDS AND THEIR USE

CROSS-REFERENCE TO RELATED APPLICATIONS

This application is a divisional of U.S. patent application Ser. No. 14/570,443, filed Dec. 15, 2014, which is a divisional of U.S. patent application Ser. No. 14/080,340, filed Nov. 14, 2013, now U.S. Pat. No. 8,911,645, which is a divisional of U.S. patent application Ser. No. 13/178,855, filed Jul. 8, 2011, now U.S. Pat. No. 8,617,426, which is a divisional of U.S. patent application Ser. No. 12/111,326, filed Apr. 29, 2008, now U.S. Pat. No. 7,981,324, which claims foreign priority to European Patent Application No. 07008747.3, filed Apr. 30, 2007. Each of these applications is incorporated herein by reference.

BACKGROUND OF THE INVENTION

The present invention relates to oxocarbon-, pseudooxocarbon- and radialene compounds as well as to their use as organic doping agent for doping an organic semiconductive matrix material for changing its electrical properties, as blocker material as well as charge injection layer and as electrode material. The invention also relates to organic semiconductive materials as well as to electronic components in which the oxocarbon-, pseudooxocarbon- and radialene compounds are used.

In the present application alicyclics in which all ring atoms are sp2-hybridized and to the extent possible carry exocyclic C—C double bonds are designated as radialenes, see also H. Hopf and G. Maas, Angew. Chem. (1992), 8, 955. Oxocarbon- and pseudooxocarbon compounds are sufficiently known as non-benzoid aromatics, see, e.g., G. Seitz, Nachr. Chem. Tech. Lab. 28 (1980), pages 804-807. The first oxocarbon compound, potassium croconate, was produced by L. Gmelin in 1825 from potash and coal. Those compounds, in which at least one oxygen atom is replaced by another heteroatom, are designated as pseudooxocarbons, as is readily known to an expert in the art.

It has been known for several years that organic semiconductors can be heavily influenced regarding their electrical conductivity by doping. Such organic semiconductive matrix materials can be built up either from compounds with good electron donor properties or from compounds with good electron acceptor properties. Strong electron acceptors such as tetracyanoquinonedimethane (TCNQ) or 2,3,5,6-tetrafluoro-tetracyano-1,4-benzoquinonedimethane (F4TCNQ) have become known for the doping of electron donor materials (HT), M. Pfeiffer, A. Beyer, T. Fritz, K. Leo, Appl. Phys. Lett., 73 (22), 3202-3204 (1998). and J. Blochwitz, M. Pfeiffer, T. Fritz, K. Leo, Appl. Phys. Lett., 73 (6), 729-731 (1998). They generate so-called holes by electron transfer processes in electron donor-like base materials (hole transport materials) by the number and mobility of which holes the conductivity of the base material is more or less significantly changed. For example, N,N'-perarylated benzidines TPD or N,N',N"-perarylated starburst compounds such as the substance TDATA, or, however, also certain metal phthalocyanines, such as in particular zinc phthalocyanine ZnPc are known as matrix material with hole transport properties.

However, the previously described compounds have disadvantages for a technical use in the production of doped semiconductive organic layers or of corresponding electronic components with such doped layers since the manufacturing processes in large-scale production plants or those on a technical scale can not always be sufficiently precise, which results in high control- and regulating expense within the processes for achieving a desired product quality or in undesired tolerances of the products. Furthermore, there are disadvantages in the use of previously known organic donors with regard to electronic components such as light-emitting diodes (OLEDs), field effect transistors (FET) or solar cells themselves since the cited production difficulties in the handling of the doping agents can lead to undesired irregularities in the electronic components or in undesired ageing effects of the electronic components. However, it should be considered at the same time that the doping agents to be used have extremely high electron affinities (reduction potentials) and other properties suitable for the application case since, e.g., the doping agents also co-determine the conductivity or other electrical properties of the organic semiconductive layer under given conditions. The energetic positions of the HOMO of the matrix material and of the LUMO of the doping agent are decisive for the doping effect.

The present invention has the task of overcoming the disadvantages of the state of the art, in particular to make new organic mesomeric compounds available that can be used in particular as doping agent for the doping of organic semiconductors, that can furthermore be more readily handled in the production process and that result in electronic components whose organic semiconductive materials can be reproducibly manufactured This task is solved, at least in part, by the following organic mesomeric compound and/or the use of the organic mesomeric compound as organic doping agent for the doping of an organic semiconductive matrix material, as blocker layer, as charge injection layer or as organic semiconductor itself, characterized in that the mesomeric compound is an oxocarbon-, pseudooxocarbon- or radialene compound with the following formula:

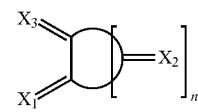

in which n=1-4; each $X_1$, $X_2$, $X_3$, $X_4$, and $X_5$ is independently selected from the group consisting of $C(CN)_2$, $(CF_3)C(CN)$, $(NO_2)C(CN)$, $C(halogen)_2$, $C(CF_3)_2$, NCN, O, S, $NR_1$,

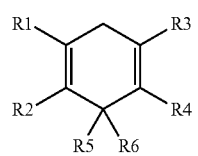

A

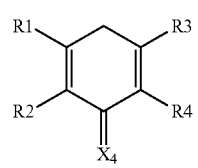

B

-continued
C
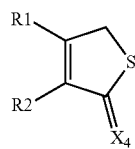
D
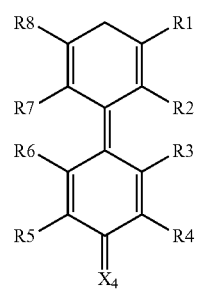
E
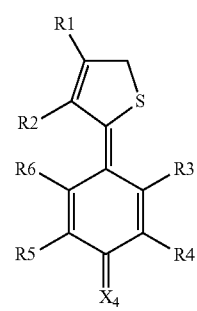
F
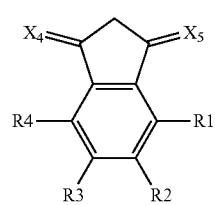
G
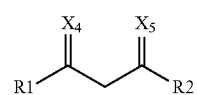
H
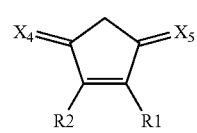
I
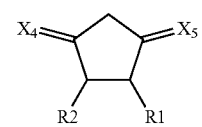
J
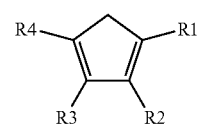
-continued
K
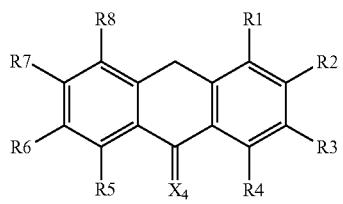
L
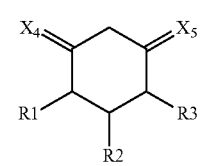
M
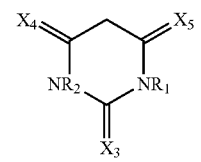
N
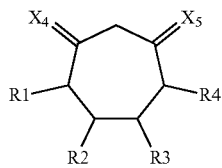
O
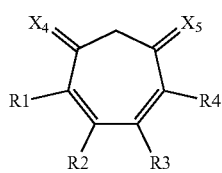
P
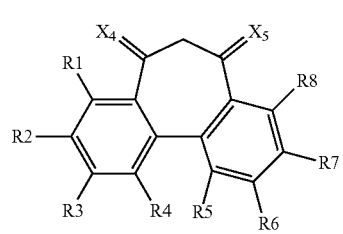
Q
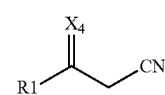
R
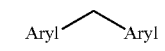
S
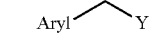
T
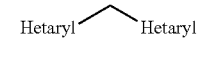
U
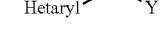
V
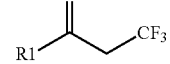
W
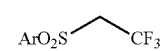

-continued

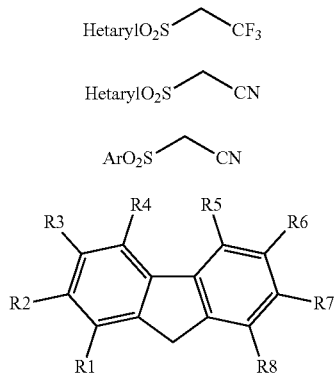

in which Y=CN, NO$_2$, COR$_1$ or is perhalogenated alkyl; aryl or Ar is a substituted or unsubstituted, aromatic hydrocarbon or biaryl, optionally polycyclic; hetaryl is a substituted or unsubstituted aromatic heterocyclic compound or biheteroaryl, preferably electron-poor, optionally polynuclear or partially or completely hydrogenated or fluorinated; and R$_1$-R$_8$ are independently selected from hydrogen, halogen, CN, NO$_2$, COR$_1$, alkyl, alkoxy, aryl and heteroaryl. In one embodiment, Y is perfluoroalkyl, including, for example, CF$_3$. In another embodiment, aryl or Ar is partially or completely hydrogenated, or partially or completely fluorinated. In a further embodiment, hetaryl is selected from pyridyl, pyrimidyl, triazine, or oxadizole. In a still further embodiment, R1-R8 are independently selected from perhalogenated and/or partially halogenated alkyl groups, including, for example, perfluorinated alkyl groups.

DETAILED DESCRIPTION

In the compounds in accordance with the invention the position of the LUMO is so low that further technically interesting hole transport materials can now be efficiently doped for the first time. Due to the extremely low position of the LUMO and to the associated high reduction potential of the compounds even performance efficiencies of solar cells can be significantly improved. In addition, these compounds are extremely diffusion-stable in organic layers on account of their high polarity. The production processes can be better controlled and thus be carried out with lesser expense and in a more reproducible manner by higher evaporation temperature and lower volatility under the same conditions, whereby, by making available oxocarbons, pseudooxocarbons and radialenes as doping agents, these make possible a sufficient electrical conductivity of the organic semiconductive matrix given advantageous electron affinity of the doping agents in the particular components at low diffusion coefficients that ensure a component structure that is uniform in time. Furthermore, the charge carrier injection of contacts into the doped layer can be improved by the doping agents. Furthermore, the doped organic semiconductive material and the resulting electronic component can have an improved long-time stability on account of the compounds used in accordance with the invention. This concerns, e.g., a reduction of the doping concentration over time. This furthermore concerns the stability of the doped layer that is arranged adjacent to non-doped layers of an electro-optical component so that electro-optical components with increased long-time stability of the electro-optical properties such as light yield at a given length, effectiveness of a solar cell or the like result.

The evaporation rate of a substrate with the compound used in accordance with the invention can be determined, e.g., using a quartz thickness monitor, as is customarily used, e.g., in the production of OLEDs. In particular, the ratio of the evaporation rates of matrix materials and doping agent can be measured by independent measurements of them using two separate quartz thickness monitors in order to adjust the doping ratio.

It is understood that the compounds used in accordance with the invention are preferably such that they evaporate more or less or practically non-decomposed. However, if necessary, even purposeful precursors can be used as doping source that release the compounds used in accordance with the invention, e.g., acid addition salts, e.g., of a volatile or non-volatile inorganic or organic acid, or their charge transfer complexes, which acids and/or electron donors are preferably not volatile or only slightly volatile or the charge transfer complex itself acts as doping agent.

The doping agent is preferably selected in such a manner that it generates a conductivity just as high as or preferably higher than F4TCNQ under conditions that are otherwise the same such as, in particular, doping concentration (molar ratio, doping agent:matrix, layer thickness, current strength) at a given matrix material (e.g., zinc phthalocyanine or another matrix material cited further below), e.g., a conductivity (s/cm) greater than/equal to 1.1 times, 1.2 times or greater than/equal to 1.5 times or twice that of F4TCNQ as doping agent.

The doping agent used in accordance with the invention is preferably selected in such a manner that the semiconductive organic material doped with it still has ≥20%, preferably ≥30%, especially preferably ≥50% or 60% of the conductivity (s/cm) of the value at 100° C. after a temperature change of 100° C. to RT (20° C.).

A few preferred oxocarbons, pseudooxocarbons and radialenes will be shown in the following that can be used with advantage for the purposes of the invention:

Derivatives of [3] radialenes

1

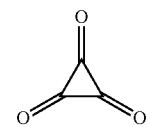

2

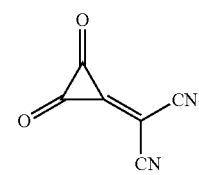

3

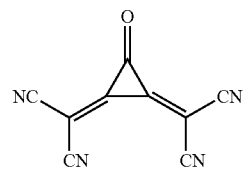

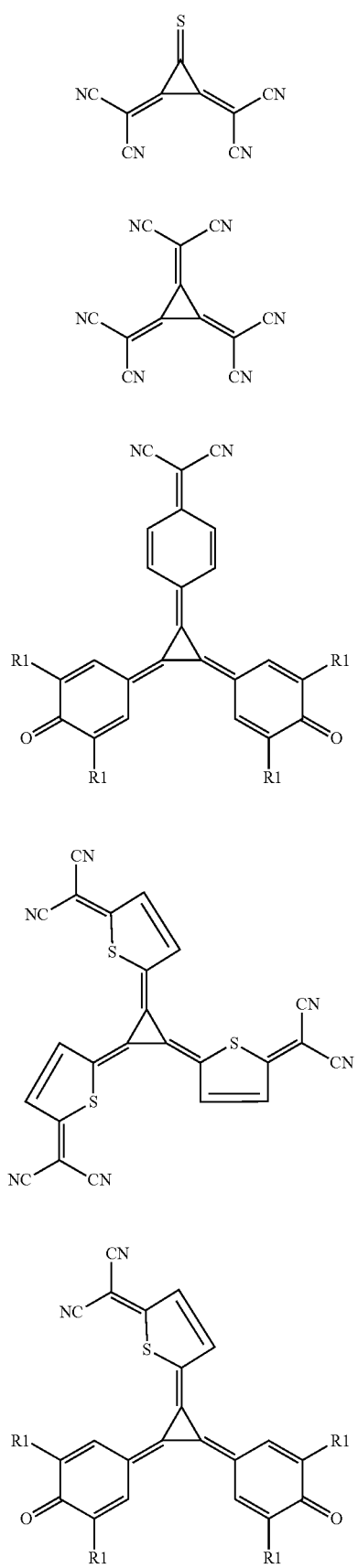
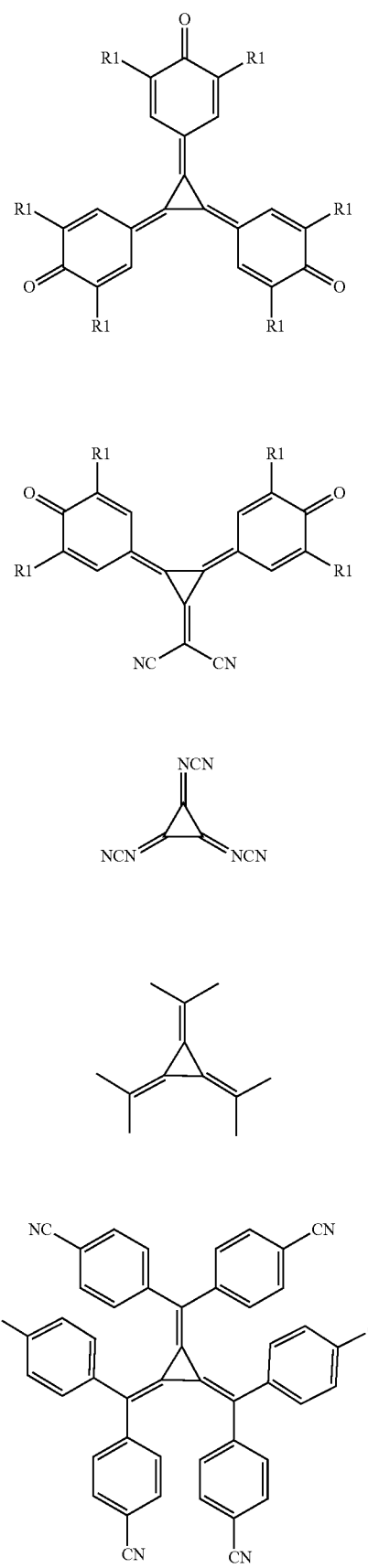

13
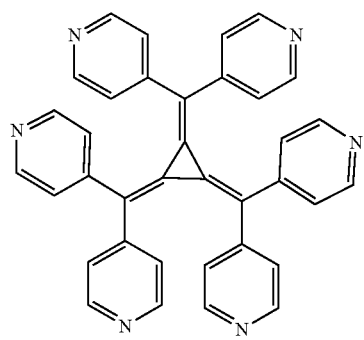
Derivatives of [4] radialenes
21
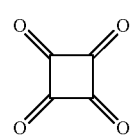
22
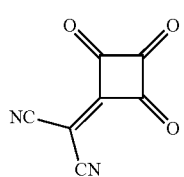
23
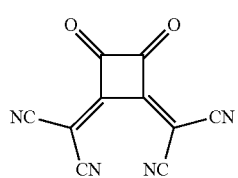
24
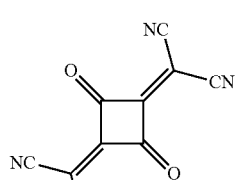
25
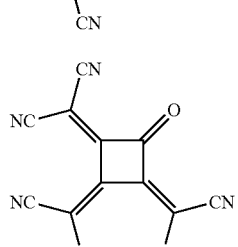
26
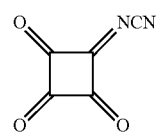
27
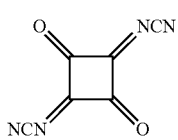
28
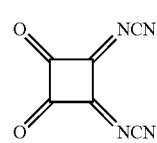
29
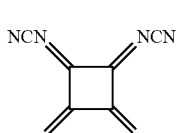
30
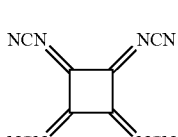
31
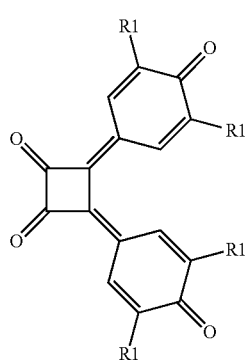
32
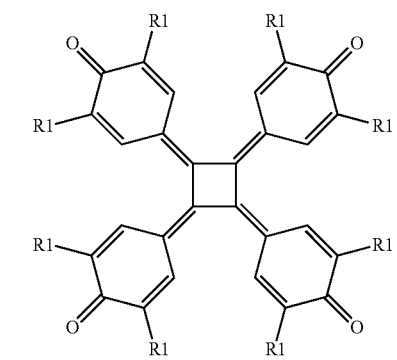
33
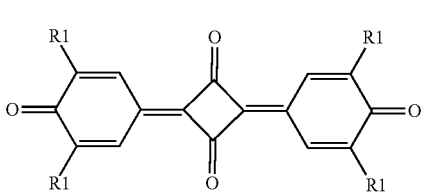

-continued

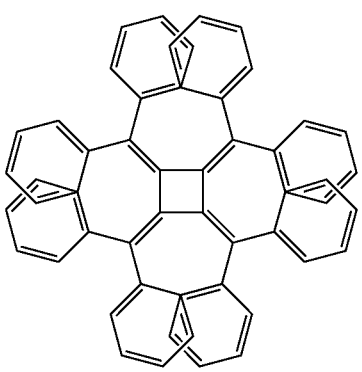

Derivatives of [5] radialenes

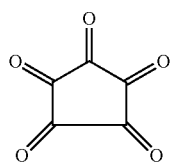

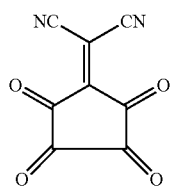

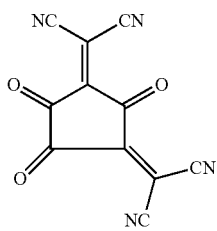

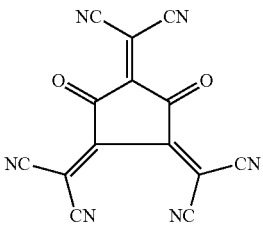

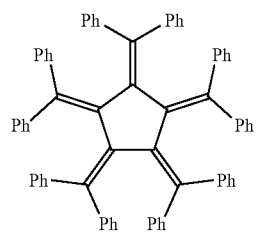

R1 = methyl, isopropyl, t-butyl

Further Derivatives of Oxocarbon-, Pseudooxocarbon- and [6] Radialene Structures

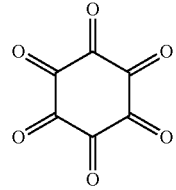

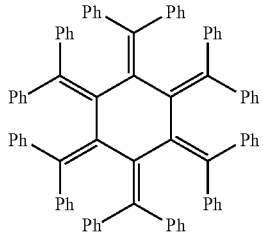

Preparation of the Oxocarbon-, Pseudooxocarbon- and Radialene Structures

The first oxocarbon compound, potassium croconate, was produced by L. Gmelin in 1825 from potash and coal. Oxocarbons and their esters and halogenides preferably react with electron-rich compounds such as aliphatic and aromatic amines, aromatics and heteroaromatics. A. H. Schmidt, Synthesis (1980) 961. The reaction products from tetrachlorocyclopropene and phenols in the presence of Lewis acids or CH-acidic compounds by strong bases, such as, e.g., arylacetonitriles, 1,3-diketones, cyclopentadienes, malonodinitriles, acceptor-substituted diarylmethanes, electron-poor diheteroarylmethanes are especially suitable for applications in accordance with the invention. [3] Radialenes are obtained after oxidation has taken place, R. West et al. J. Org. Chem. (1975) 40 2295; T. Kazuka, T. Shinji J. Chem. Soc. Chem. Commun. (1994) 519; T. Fukunaga et al. JACS (1976) 98 610.

Squaric acid dichloride and phenols, that can subsequently be oxidized to 4 [radialenes] are furthermore also very well-suited, R. West, S. K. Koster J. Org. Chem. (1975) 40 2300; the nucleophilic anion of the CH-acidic melonic acid dinitrile can also be substituted with preference with esters under the splitting off of alcohol to dianionic squaric acid compounds, T. Fukanaga J. Am. Chem. Soc. (1976) 98 610; W. Ziegenbein, H.-E. Sprenger Angew. Chem. (1967) 79 581; G. Seitz et al. Chem. Ber. (1987) 120 1691. The oxidation of these CN-substituted compounds was successful only electrochemically in the past, T. A. Blinka, R. West, Tetrahedron Lett. (1983) 24 1567. [4] Radialenes can also be prepared by thermal dimerization of diquinone ethylenes, R. West, S. K. Koster, JOC (1975) 40 2300.

The first croconic acid derivatives that were substituted with malodinitrile were able to be produced by Fatiadi, J. Org. Chem. (1980) 45 1338, J. Am. Chem. Soc. (1978) 100 2586. The oxidation of these compounds was also examined electrochemically by him, A. J. Fatiadi, L. M. Doane, J. Electroanal. Chem. (1982) 135 193-209.

However, even [6] radialenes are known, H. Hopf, A. K. Wick Helv. Chim. Acta (1961) 46 380-6.

A few later representatives were and/or are used in the electrophotography as electroluminescent material in video screens, as dye, as photoconductors, as organic oxidants, U.S. Pat. No. 4,003,943 (1977), JP 07-168377, JP 2004010703 A (2004), U.S. Pat. No. 4,133,821 (1979).

Preparation of New Cyclic Oxocarbon- and Pseudooxocarbon Derivatives

Example a) 1,3-Bis(dicyanomethylene)indane-2-ylidene-bis (4-oxo-[3,5-di-t-butyl]-2,-5-cyclohexadienylidene)- cyclopropane 4.75 g bis(4-oxo-[3,5-di-t-butyl]-2,5-cyclohexadienyl)- cyclopropenone, 3.5 g 1,3-bis(dicyanomethylene)-indane as well as 60 mg β-alanine are dissolved in 12 ml acetic anhydride and briefly heated on the reflux under stirring. The mixture is compounded with 60 ml toluene, allowed to cool off and the reddish-brown crystalline solid removed by suction. The mixture is subsequently washed with benzene/ toluene and recrystallized.

Yield: 4.6 g 2.5 g of the reddish-brown crystals are dissolved under argon in 100 ml chloroform and united with a solution of 4.7 g red potassium ferrocyanide and 8.8 g KOH in 150 ml water. After 1 h intensive stirring, the organic phase is dried with Na2SO4 and evaporated to low bulk and the product recrystallized.

Yield: 2.3 g blackish-green crystals fp.>250° C. under decomposition b) (2E,2'E,2"E)-2,2',2"-(cyclopropane-1,2,3-tri- ylidene)tris(2-pentafluor-ophenylacetonitrile)

A solution of 4 g (20 mmol) pentafluorophenylacetonitrile in 10 ml glyme are added dropwise to 1.6 g NaH in 40 ml glyme and cooled with icewater. Subsequently a solution of 0.9 tetrachloro cyclopropene in 10 ml glyme was added dropwise. After stirring for 24 h at room temperature the dark mixture is poured onto ice water and is extracted with CHCl$_3$. The extracts provide a black solid.

4 g of the raw intermediate product are dissolved in 50 ml CHCl$_3$, and to this solution 50 ml water, containing 2 g K$_2$CO$_3$, is added. 0.5 ml bromine is added to this dark green 2-phase mixture under stirring. Thereafter, the phases are separated, and the organic phase is evaporated after drying over Na2SO4 using a rotatory evaporator. A remaining orange solid is recrystallized using a suitable solvent. Yield: about 70%.

FP: 182° C.

c) (2E,2'E,2"E)-2,2',2"-(cyclopropane-1,2,3-tri- ylidene)tris(2-[2',3',5',-6'-tetrafluoropyrid-4'-yl]ac- etonitrile)

4.75 g 2,3,5,6-tetrafluoropyridyl actonitrile in 10 ml glyme is added dropwise to 0.4 g LiH in 60 ml glyme. Thereafter 1.1 g tetrachlorocyclopropene is added dropwise to the solution and is stirred over night. The mixture is poured onto ice-water and is extracted with EtOAc. After drying the extracts and evaporation 4.6 g of a solid remained.

2.25 g of the solid is dissolved in 50 ml AcOH, and 5 ml HNO$_3$ (65%) is added. Water is added to this orange-brown solution, and the precipitate obtained is isolated, washed with water and dried. Yield: 1 g. Fp: 170° C.

d) (2E,2'E,2"E)-2,2',2"-(cyclopropane-1,2,3-tri- ylidene)tris(2-(2,6-dichl-oro-3,5-difluoro-4-(trisfluo- romethyl)phenyl)acetonitrile)

0.29 g LiH are suspended in 68 ml glyme, and cooled, and 5 g 2,6-dichloro-3,5-difluoro-4-(trifluoromethyl)phenyl)ac- etonitrile) in 6 ml glyme are added slowly under argon atmosphere. The mixture is heated to room temperature, and 0.8 g tetrachlorocyclopropene are added dropwise, and the mixture is stirred over night. The solution is poured onto ice-water, the precipitate obtained is isolated and dried. Yield: 4.75 g.

3.5 g of the product is dissolved in glacial acetic acid, and under cooling 7 ml HNO$_3$ is dropwise added, subsequently water is added, and the precipitate obtained is isolated. The product is recrystallized utilizing a suitable solvent. Yield: 72%. Fp.: 185° C.

e) (2E,2'E,2"E)-2,2',2"-(cyclopropane-1,2,3-tri- ylidene)tris(2-(2,3,5,6-t-etrafluoro-4-cyano-pheny- lacetonitrile)(2-2,3,5,6-tetrafluoro-4-trifluorome- thyl-phenylacetonitrile)

Internal salt: 2,3-bis(cyano(4-cyano-2,3,5,6-tetrafluoro- phenyl)methyl)-1-triethylamino)c-yclopror-2-ene-1-ide.

5.34 g tetrachlorocyclopropene and 13.8 g 2,3,5,6-tetra- fluoro-4-cyanobenzylcyanid in 300 ml CH$_2$Cl$_2$ are cooled, and 17.1 g triethylamine is added. The resultant product is stirred and heated to room temperature. Then water is added, and the yellow solid obtained is removed, washed and dried at air. Yield: 93%.

1.15 g 2,3,5,6-tetrafluoro-4-(trifluoromethyl)-benzylcya- nid in 15 ml THF is dropwise added to 0.46 g LDA in 55 ml THF. The solution is cooled, and a suspension of 2 g of the internal salt in DMPU is added dropwise. The solution is poured into ice-water. The precipitate is removed and washed with water and subsequently dried in vacuo. Yield: 100%.

2.7 g of the material to be oxidized is dissolved in 70 ml AcOH, and 5.5 ml HNO$_3$ (65%) is added dropwise. The material to be oxidized is then precipitated with water. After isolation, washing with water and drying in vacuo the product is obtained in a yield of 90%. Fp: >250° C.

f) (2E,2'E,2"E,2'"E)-2,2',2",2'"-(cyclopropane-1,2,3, 4-tetraylidene)te-trakis(2-2',3',5',6'-tetrafluoro-4'- cyanophenyl)acetonitrile 1.2 g 1,2-bis-tosyl-3,4-bis-dimethylamino-quadratat is heated with 2.14 g 2,3,5,6-tetrafluoro-4-cyano-benzylcyanid in 20 ml pyridin for 16 h with stirring. The solution is concentrated and given into ice-water. Thereafter it is extracted with EtOAc. Concentrating the dried extracts results in the product which can be recrystallized in a suitable solvent. Fp.: >250° C.

Matrix Materials

The present invention describes suitable doping agents for organic semiconductive materials such as hole transport materials HT that are customarily used in OLEDs or organic solar cells. The semiconductive materials are preferably intrinsically hole-conducting. The following can apply to doping agents of the oxocarbon- and pseudooxocarbon types in accordance with the invention.

The matrix material can consist partially (>10 or >25% by weight) or substantially (>50% by weight or >75% by weight) or totally of a metal phthalocyanine complex, a porphyrine complex, especially metal porphyrine complex, oligothiophene-, oligophenyl-, oligophenylene vinylene- or oligofluorene compound, in which the oligomer preferably comprises 2-500 or more, preferably 2-100 or 2-50 or 2-10 or more monomeric units. The oligomer can also comprise >4, >6 or >10 or more monomeric units, in particular also for the above-indicated ranges, thus, e.g., 4 or 6-10 monomeric units, 6 or 10-100 monomeric units or 10-500 monomeric units. The monomers and oligomers can be substituted or unsubstituted and even block- or mixed polymerizates of the cited oligomers can be present as well as a compound with a triarylamine unit or a spiro-bifluorene compound. The cited matrix materials can also be present in combination with each other, optionally also in combination with other matrix materials. The matrix materials can have electron-donating substituents such as alkyl- or alkoxy groups that have a reduced ionizing energy or reduce the ionizing energy of the matrix material.

The metal phthalocyanine complexes or porphyrine complexes used as matrix material can have a main group metal atom or subgroup metal atom. The metal atom Me can be coordinated 4-, 5- or 6-fold, e.g., in the form of oxo- (Me=O), dioxo- (O=Me=O) imine-, diimine-, hydroxo-, dihydroxo-, amino- or diamino complexes, without being limited to them. The phthalocyanine complex or porphyrine complex can each be partially hydrogenated, however, the mesomeric ring system is preferably not disturbed. The phthalocyanine can contain, e.g., magnesium, zinc, iron, nickel, cobalt, magnesium, copper or vanadyl (=VO) as central atom. The same or other metal atoms or oxometal atoms can be present in the case of porphyrine complexes.

In particular, such dopable hole transport materials HT can be arylated benzidines, e.g., N,N'-perarylated benzidines or other diamines such as of the type TPD (in which one, several or all of the aryl groups can have aromatic heteroatoms), suitable arylated starburst compounds such as N,N', N"-perarylated starburst compounds such as the compound TDATA (in which one, several or all of the aryl groups can have aromatic heteroatoms). The aryl groups can comprise phenyl, naphthyl, pyridine, quinoline, isoquinoline, peridazine, pyrimidine, pyrazine, pyrazole, imidazole, oxazole, furan, pyrrole, indole or the like, especially for each of the above-cited compounds. The phenyl groups of the particular compounds can be partially or completely replaced by thiophene groups.

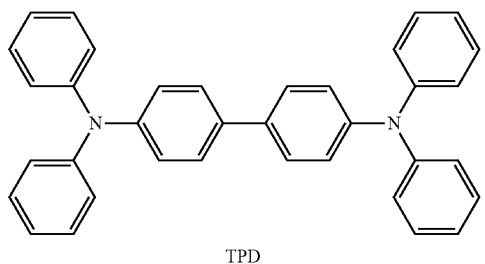

TPD

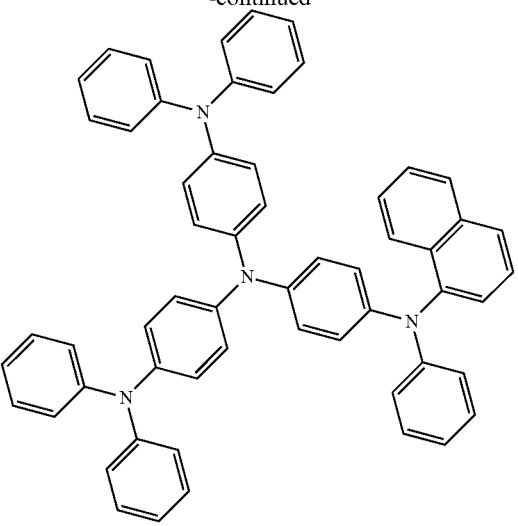

TDATA

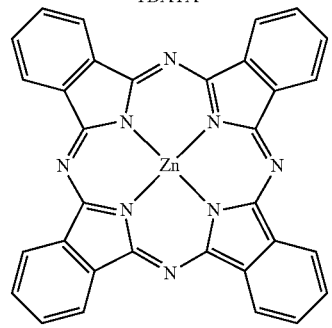

ZnPc

The material used preferably consists completely of a metal phthalocyanine complex, a porphyrine complex, a compound with a triarylamine unit or a spiro-bifluorene compound.

It is understood that even other suitable organic matrix materials, in particular hole-conducting materials can be used that have semiconductive properties.

Doping

The doping can take place in particular in such a manner that the molar ratio of matrix molecule to doping agent, or in the case of oligomeric matrix materials the ratio of matrix monomer number to doping agent is 1:100000, preferably 1:10000, especially preferably 1:1 to 1:100000, e.g., 1:5 to 1:1000, e.g., 1:10 to 1:100, e.g., ca. 1:50 to 1:100 or also 1:25 to 1:50.

Evaporation of the Doping Agents

The doping of the particular matrix material (preferably indicated here as hole-conducting matrix material HT) with the doping agents to be used in accordance with the invention can be produced by one or a combination of the following processes:

a) Mixed evaporation in the vacuum with a source for HT and one for the doping agent.

b) Sequential deposition of HT and doping agent with subsequent inward diffusion of the doping agent by thermal treatment c) Doping of an HT layer by a solution of doping agent with subsequent evaporation of the solvent by thermal treatment d) Surface doping of an HT layer by a layer of doping agent applied on the surface.

The doping can take place in such a manner that the doping agent is evaporated out of a precursor compound that releases the doping agent under heating and/or irradiation. The irradiation can take place by electromagnetic radiation, especially visible light, UV light or IR light, e.g., by laser light or also by other radiation types. The heat necessary for evaporation can substantially be made available by the irradiation and can also be radiated in a purposeful manner into certain bands of the compounds or precursors or compound complexes such as charge transfer complexes to be evaporated in order to facilitate the evaporation of the compounds by dissociation of the complexes by conversion into excited states. It is understood that the evaporation conditions described in the following are directed to those without irradiation and that uniform evaporation conditions are to be used for purposes of comparison.

For example, the following can be used as precursor compounds:

a) Mixtures or stoichiometric or mixed crystalline compounds of the doping agent and an inert, non-volatile substance, e.g., a polymer, molecular sieve, aluminum oxide, silica gel, and oligomers or another organic or inorganic substance with high evaporation temperature, in which the doping agent is bound primarily by van der Waals forces and/or hydrogen bridge bonding to this substance.

b) Mixture or stoichiometric or mixed crystalline compound of the doping agent and one non-volatile compound V more or less of the electron donor type, in which a more or less complete charge transfer occurs between the doping agent and the compound V as in charge transfer complexes with more or less electron-rich polyaromatics or heteroaromatics or another organic or inorganic substance with high evaporation temperature.

c) Mixture or stoichiometric or mixed crystalline compound of the doping agent and a substance that evaporates together with the doping agent and has the same or higher ionizing energy as the substance HT to be doped, so that the substance does not form a trap for holes in the organic matrix material. According to the invention the substance can also be identical to the matrix material here, e.g., be a metal phthalocyanine or benzidine derivative. Further suitable volatile co-substances such as hydroquinones, 1,4-phenylene diamines or 1-amino-4-hydroxybenzene or other compounds form quinhydrones or other charge transfer complexes.

Electronic Component

A plurality of electronic components or equipment containing them can be produced using the organic compounds in accordance with the invention for producing doped organic semiconductive materials that can be arranged in particular in the form of layers or electrical line paths. In particular, the doping agents in accordance with the invention can be used to produce organic, light-emitting diodes (OLED), organic solar cells, organic diodes, especially those with a high rectification ratio such as $10^3$-$10^7$, preferably $10^4$-$10^7$ or $10^5$-$10^7$ or organic field effect transistors. The conductivity of the doped layers and/or the improvement of the charge carrier injection of contacts into the doped layer can be improved by the doping agents in accordance with the invention. In particular in the case of OLEDs the component can have a pin structure or an inverse structure without being limited to them. However, the use of the doping agents in accordance with the invention is not limited to the advantageous exemplary embodiments cited above.

EXEMPLARY EMBODIMENTS

The invention will be explained in detail with a few exemplary embodiments.

The compounds to be used in accordance with the invention, in particular, the previously indicated exemplary compounds from the previously described substance class of the oxocarbon- and of the pseudooxocarbon compounds will now be used in the following manner as doping agents for different hole conductors that for their part are used for constructing certain microelectronic or optoelectronic components such as, e.g., an OLED. The doping agents can be evaporated at the same time adjacent to one another with the hole transport materials of the matrix in the high vacuum (ca. $2\times10^{-4}$ Pa) at elevated temperatures. A typical substrate evaporation rate for the matrix material is 0.2 nm/s (density ca. 1.5 g/cm$^3$). The evaporation rates for the doping agents can vary between 0.001 and 0.5 nm/s at the same assumed density in accordance with the desired doping ratio.

In the following examples the current measurements were carried out over a current path of the doped HT material 1 mm long and ca. 0.5 mm wide at 1V. under these conditions ZnPc conducts practically no electrical current.

EXAMPLES

Example 1

Doping of ZnPc with dicyanomethylenebis(4-oxo-[3,5-di-t-butyl]-2,5-cyclohexadienylidene)cyclopropane Conductivity: $1.5\times10^{-5}$ s/cm Example 2

Doping of spiro-TTP with dicyanomethylenebis(4-oxo-[3,5-di-t-butyl]-2,5-cyclohexadienylidene)cyclopropane Conductivity: 3, $6\times10^{-7}$ s/cm Example 3

Doping of ZnPC with 1,3-bis(dicyanomethylene)indane-2-ylidene-bis(4-oxo-[3,5-di-t-butyl]-2,5-cyclohexadienylidene)cyclopropane Conductivity: $5.8\times10^{-6}$ s/cm Example 4

Doping of spiro-TTP with 1,3-bis(dicyanomethylene)indane-2-ylidene-bis(4-oxo-[3,5-di-t-butyl]-2,5-cyclohexadienylidene)cyclopropane conductivity: $5\times10^{-7}$ S/cm Example 5

Doping of $N^4$, $N^4$-(biphenyl-4,4%-diyl)bis($N^4$,$N^4$, $N^{4'}$-triphenylbiphen-yl-4,4'-diamine) with (2E,2'E, 2''E)-2,2',2''-(cyclopropane-1,2,3-triyliden)tris(2-pentafluoroph-enylacetonitrile 10%

Conductivity: $3.21\times10^{-6}$ S/cm

Example 6

Doping of Spiro-TTP with (2E,2'E,2"E)-2,2',2"-cyclopropane-1,2,3-triylidene)tris(2-pentafluorophenylacetonitrile) 10%

Conductivity: $1.89 \times 10^{-6}$ S/cm.

Example 7

Doping of 4,4'-bis(10,11-dihydro-5H-dibenzo[b,f]azepine-5-yl)biphenyl with (2E,2'E,2"E)-2,2',2"-(cyclopropane-1,2,3-triylidene)tris(2-pentafluorophenylacetonitrile) 10%

Conductivity: $1.55 \times 10^{-7}$ S/cm.

Example 8

Doping of Spiro-TTP with (2E,2'E,2"E)-2,2',2"-(cyclopropane-1,2,3-triylidene)tris(2-[2',3',5',6'-tetrafluoropyrid-4'-yl]acetonitrile) 5%

Conductivity: $4.35 \times 10^{-5}$ S/cm.

Example 9

Doping of a-NPD with (2E,2'E,2"E)-2,2',2"-cyclopropane-1,2,3-triylidene)tris(2-[2',3',5',6'-tetrafluoropyrid-4'-yl]acetonitrile) 5%

Conductivity: $1.28 \times 10^{-5}$ S/cm.

Example 10

Doping of ZnPc with (N,N',N",N'''-cyclobutane-1,2,3,4-tetraylidene)tetraaniline 5%

Conductivity: $1.3 \times 10^{-6}$ S/cm.

Example 11

Doping of spiro-TTP with (2E,2'E,2"E,2'''E)-2,2',2",2'''-(cyclobutane-1,2,3,4-tetraylidene)N,N',—N",N'''-cyclobutane-1,2,3,4-tetraylidene)tetrakis(2-perfluorophenyl)aceto-nitrile) 5%

Conductivity: $3.3 \times 10^{-5}$ S/cm.

The features of the invention disclosed in the previous description and in the claims can be essential individually as well as in any combination for the realization of the invention in its various embodiments.

The invention claimed is:

1. A charge injection layer comprising an organic semiconductive matrix material and an organic doping agent, wherein the organic doping agent comprises an organic mesomeric compound, wherein the organic mesomeric compound comprises an oxocarbon-, pseudooxocarbon-, or radialene compound with the following formula:

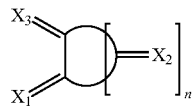

wherein n=1-4; each X1, X2, and X3 is independently selected from the group consisting of C(CN)2, (CF3)C(CN), (NO2)C(CN), C(halogen)2, C(CF3)2, NCN, O, S, NR1,

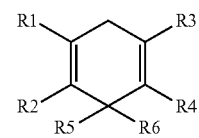
A

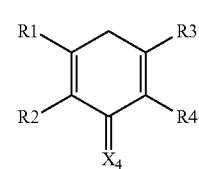
B

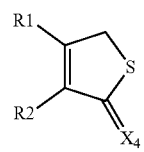
C

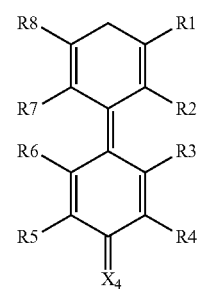
D

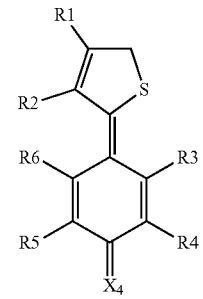
E

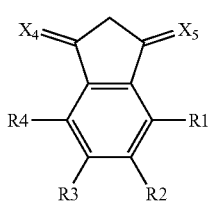
F

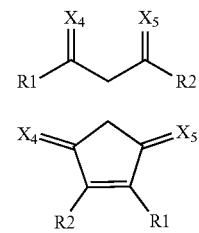
G

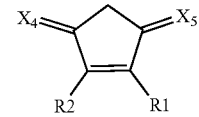
H wherein X4 and X5 are independently selected from the group consisting of C(CN)2, (CF3)C(CN), (NO2)C(CN), C(halogen)2, C(CF3)2, CN, O, S, and NR1,
wherein Y=CN, NO2, COR1, or a perhalogenated alkyl; aryl or Ar is a substituted or unsubstituted aromatic hydrocarbon or biaryl; hetaryl is a substituted or unsubstituted aromatic heterocyclic compound or biheteroaryl; and R1-R8 are independently selected from hydrogen, halogen, CN, NO2, COR1, alkyl, alkoxy, aryl, or heteroaryl, wherein the molar doping ratio of the organic doping agent to the organic semiconductive matrix material, respectively, or the doping ratio of the organic doping agent to a monomer unit of the organic semiconductive matrix material when the organic semiconductive matrix material is a polymeric matrix molecule, is from 1:1 to 1:100000.

2. The charge injection layer according to claim 1, wherein Y is perfluoroalkyl.

3. The charge injection layer according to claim 1, wherein aryl is partially or completely fluorinated.

4. The charge injection layer according to claim 1, wherein hetaryl is selected from pyridyl, pyrimidyl, triazine, or oxadiazole.

5. The charge injection layer according to claim 1, wherein R1-R8 are independently selected from perhalogenated or partially halogenated alkyl groups.

6. An oxocarbon, pseudooxocarbon-, or radialene compound with the following formula wherein n=1-4;
wherein for n=1: each X1-X3 is independently selected from (CF3)C(CN), C(CF3)2, or one of structures A-W4

A 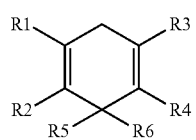
B 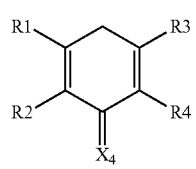
C 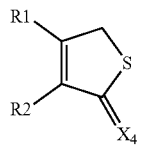
D 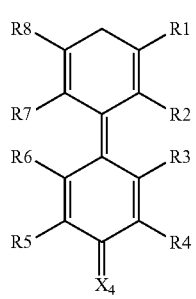
E 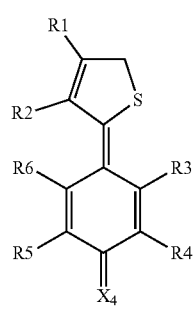
F 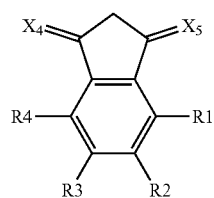
G 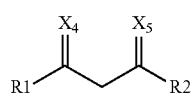
H 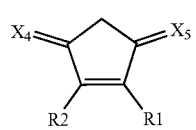
I 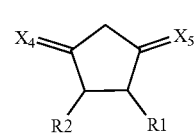
-continued
J 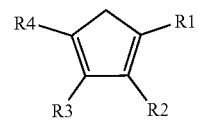
K 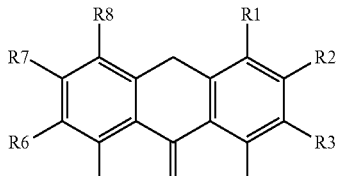
L 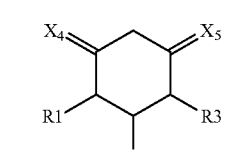
M 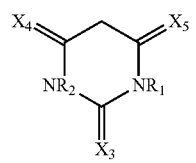
N 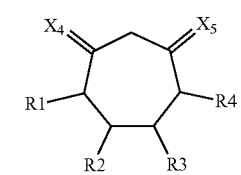
O 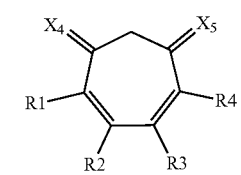
P 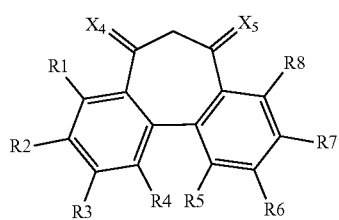
Q 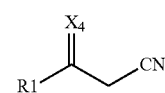
R 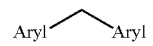
S 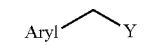
T 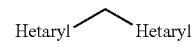
U 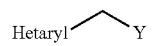

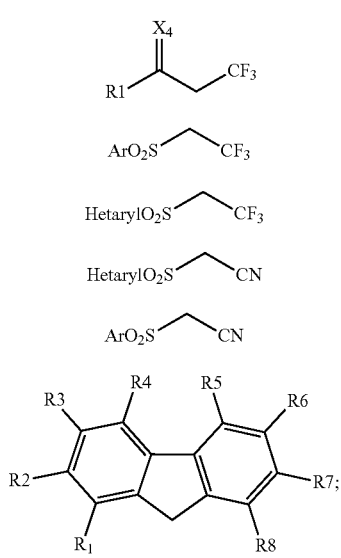

X4 and X5 are independently selected from (CF$_3$)C (CN), C(CF$_3$)$_2$, or NCN; Y is selected from CN, COR$_1$, or perhalogenated alkyl groups; aryl or Ar is selected from a substituted or unsubstituted aromatic hydrocarbon, a substituted or unsubstituted polycyclic aromatic hydrocarbon, or a substituted or unsubstituted biaryl aromatic hydrocarbon, wherein the aromatic hydrocarbon, the polycyclic aromatic hydrocarbon, or the biaryl aromatic hydrocarbon is partially or completely hydrogenated or fluorinated; hetaryl and bihetaryl are selected from a substituted or unsubstituted aromatic heterocyclic compound, a substituted or unsubstituted polynuclear aromatic heterocyclic compound, or a partially or completely hydrogenated or fluorinated heteroaromatic compound; R1-R8 are independently selected from hydrogen, halogen, CN, NO$_2$, COR$_1$, perhalogenated and/or partially halogenated alkyl groups, or substituted and/or unsubstituted aryl- or heteroaryl groups.

7. The oxocarbon, pseudooxocarbon-, or radialene compound according to claim 6, wherein hetaryl is selected from pyridyl, pyrimidyl, triazine, or oxadiazole.

8. An organic ferromagnet comprising [1] the oxocarbon-, pseudooxocarbon-, or radialene compound according to claim 6, or a radical anionic salt thereof, a dianionic salt thereof, or a charge transfer complex thereof, and [2] one or more donors.

9. An organic conductor comprising [1] the oxocarbon-, pseudooxocarbon-, or radialene compound according to claim 6, or a radical anionic salt thereof, a dianionic salt thereof, or a charge transfer complex thereof, and [2] one or more donors.

10. An organic semiconductive material comprising at least one organic matrix compound and at least one doping agent, wherein the at least one doping agent comprises the oxocarbon-, pseudooxocarbon- or radialene compound according to claim 6.

11. The organic semiconductive material according to claim 10, wherein the molar doping ratio of the at least one doping agent to the at least one organic matrix compound and/or the doping ratio of the at least one doping agent to monomeric units of the at least one organic matrix compound when the organic matrix compound is a polymeric matrix molecule is between 1:1 and 1:100,000.

12. An electronic component comprising an electronically functionally active area, wherein the electronically functionally active area comprises the oxocarbon-, pseudooxocarbon- or radialene compound according to claim 6.

13. The electronic component according to claim 12, wherein the electronically functionally active area comprises an organic semiconductive matrix material that is doped with at least one doping agent for changing the electronic properties of the organic semiconductive matrix material, wherein the at least one doping agent comprises the oxocarbon-, pseudooxocarbon- or radialene compound.

14. The electronic component according to claim 12, wherein the electronic component is an organic light-emitting diode, a photovoltaic cell, an organic solar cell, an organic diode, or an organic field effect transistor.

15. The charge injection layer according to claim 1, wherein hetaryl is electron-poor, polynuclear, partially hydrogenated, partially fluorinated, completely hydrogenated, completely fluorinated, or a combination thereof.

16. The charge injection layer according to claim 1, wherein the molar doping ratio of the organic doping agent to the organic semiconductive matrix material, respectively, or the doping ratio of the organic doping agent to a monomer unit of the organic semiconductive matrix material when the organic semiconductive matrix material is a polymeric matrix molecule, is from 1:5 to 1:1000.

17. The charge injection layer according to claim 1, wherein the perhalogenated and/or partially halogenated alkyl groups comprise perfluorinated alkyl groups.

18. The oxocarbon, pseudooxocarbon- or radialene compound according to claim 6, wherein the perhalogenated alkyl groups comprise perfluoroalkyl.

19. The oxocarbon, pseudooxocarbon- or radialene compound according to claim 6, wherein hetaryl and bihetaryl comprise an electron-poor compound, are polynuclear, partially hydrogenated, partially fluorinated, completely hydrogenated, completely fluorinated, or a combination thereof.

20. The organic semiconductive material according to claim 10, wherein the molar doping ratio of the at least one doping agent to the at least one organic matrix compound and/or the doping ratio of the at least one doping agent to monomeric units of the at least one organic matrix compound when the at least one organic matrix compound is a polymeric matrix molecule is between 1:5 to 1:1000.

* * * * *